Nov. 8, 1949. H. C. SWIM Plant Pat. 897
ROSE PLANT
Filed Aug. 12, 1948
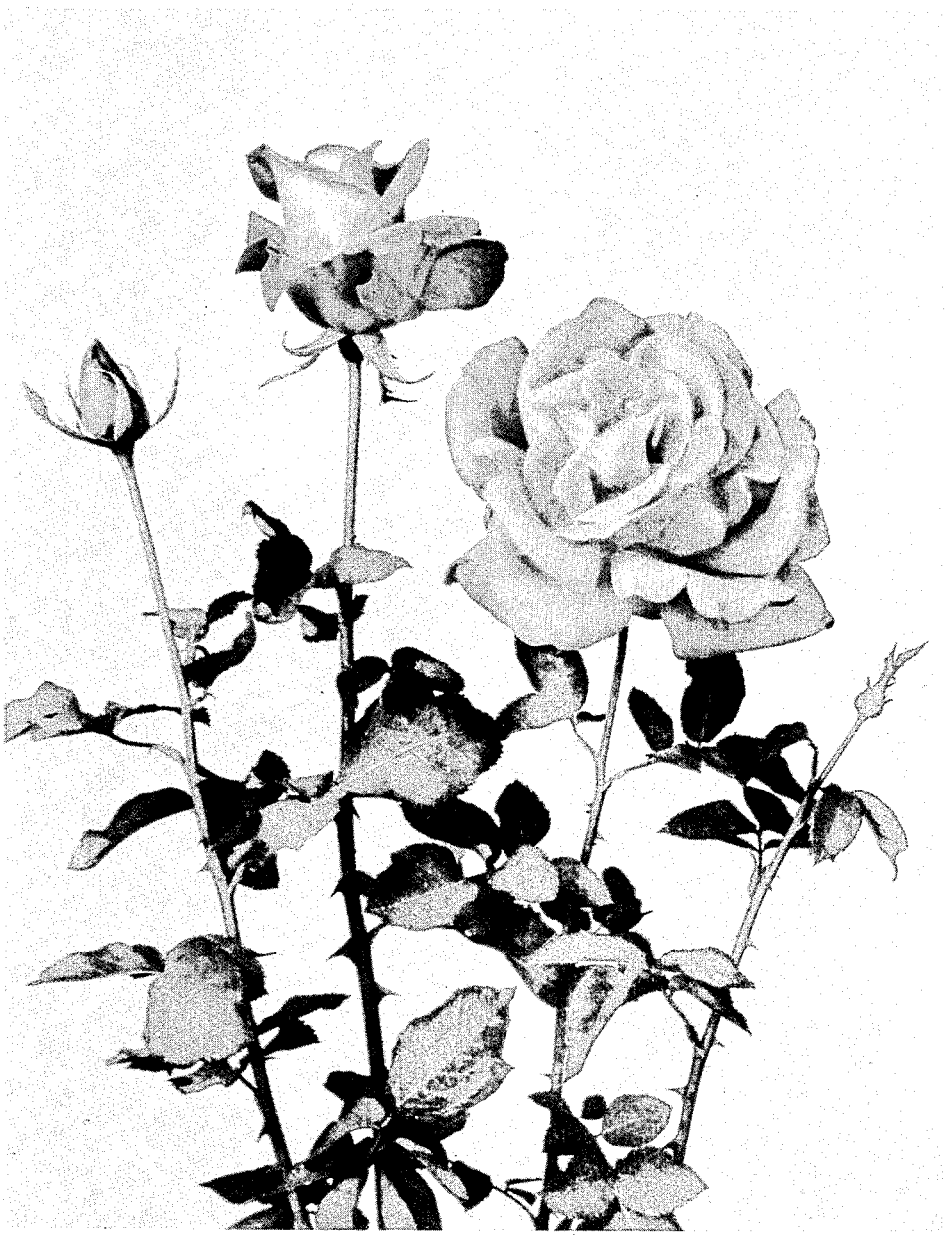
Inventor
H. C. Swim
By Robb & Robb
Attorneys Patented Nov. 8, 1949

Plant Pat. 897

UNITED STATES PATENT OFFICE

897

ROSE PLANT

Herbert C. Swim, Ontario, Calif., assignor to Armstrong Nurseries, Inc., Ontario, Calif., a corporation of California Application August 12, 1948, Serial No. 43,810

1 Claim. (Cl. 47—61)

The present invention relates to a new and distinct variety of rose plant, resulting from crossing two well-known varieties, and combining in the progeny many of the desirable characteristics of each parent.

This new variety is notable for the following distinguishing combination of characters:

(1) An exceptionally large flower for red roses.

(2) A shade of red color in the bud and newly opened bloom that to the best of my knowledge is entirely new in hybrid tea roses and the more particularly distinctive in the classe of double (petalage) roses.

(3) A flower bud of exceptional length as the first petal opens and produced on a peduncle of unusual length.

(4) Exceptionally vigorous plant on which the flowers are produced singly on stems of greater than average length.

This new variety differs importantly from its seed parent in the following respects:

(1) "Contrast" has foliage with a glossy surface, whereas this new variety has foliage of a dull surface.

(2) While both varieties are upright in habit, "Contrast" is slender, wherease this new variety has a broad, bushy habit.

(3) The flowers of "Contrast" are properly classed according to popular terms as bicolor, whereas this new variety is a red rose.

(4) This new variety has more thorns, both large and small, than its seed parent "Contrast" which is relatively thornless.

As regards its pollen parent, this new rose differs in the following manner:

(1) The flowers of this new variety are popularly classed as deep red, whereas the flowers of "Charlotte Armstrong" are classed as light red.

(2) While the bud of this new variety is classified as urn-shaped as is the bud of "Charlotte Armstrong," there is actually quite a little difference in the appearance of the buds of these two varieties. The tips of the petals of the buds of this new variety reflex sharply, whereas the tips of the petals in the opening bud of "Charlotte Armstrong" reflex only slightly.

(3) The seed of "Charlotte Armstrong" are mostly enclosed within the pericarp (calyx), whereas in this new variety the seeds are all protruding from the pericarp or outside of it.

Asexual reproduction shows that these characteristics hold true through succeeding propagations.

In the drawing, specimens of this new variety are illustrated at different stages of development of the flowers from bud to full blown blooms.

The following is a detailed description of the new variety, all references to color being in accordance with the R. F. Wilson's Horticultural Colour Chart, except where indicated to be in accordance with Ridgway's Color Standards and Nomenclature:

Type: Tall; bush; outdoor; seedling; for cut flowers and garden decoration.

Class: Hybrid tea.

Breeding: Seedling.

*Seed parent.*—"Contrast" (unpatented).

*Pollen parent.*—"Charlotte Armstrong" (Pl. Pat. #455).

Propagation: Holds its distinguishing characteristics through succeeding propagations by budding.

*Flower*

Locality where grown: Ontario, California.

Flowers borne: Singly to stem; on weak, normal to strong long stems.

Quantity of bloom: Free; outdoors.

Continuity: Almost continuous during growing season.

Fragrance: Slight; tea.

Bud:

*Peduncle.*—Unusually long; medium to heavy; sometimes bending, usually erect; almost smooth; few gland-tipped cilia and prickles. *Color*—near Absinthe Green, Plate XXXI (Ridgway), becoming washed with Prussian Red, Plate XXVII (Ridgway), on side exposed to sun.

*Before calyx breaks.—Size*—medium to large. *Form*—long; pointed; with foliaceous appendages and tomentum on the surface of the bud; with slender, much cut, bristle-like foliaceous parts extending beyond the tip of the bud equal to ¾ or more of its length.

*As calyx breaks.—Color*—Chrysanthemum Crimson, Plate 824, page 169. *Sepals*—inner surface with fine, woolly tomentum; when margins are covered by adjacent sepals they have only woolly tomentum, but when margins are not covered by adjacent sepals they have stipitate glands and woolly tomentum.

*As first petal opens.—Size*—large. *Form*—very long pointed to urn-shaped. *Color*—outside: near Currant Red, Plate 821/1, page 167, with a small spot of Canary Yellow, Plate 2/2, page 2, at base of petal; inside: near Blood Red, Plate 820, page 166, with a spot of Aureolin, Plate 3, page 3, at base of petal.

*Opening.*—Opens up well.

Bloom: Size, when fully open—large; 4 inches to 5 inches.

*Petalage.*—Double; from 24 to 30 petals; arranged regularly with 2 to 4 petaloids at center of flowers.

*Form.*—Full, high centered at first; becoming flat at maturity; petals remaining at first loosely rolled outward; becoming later, at maturity, tightly rolled outward.

Petals:

*Texture.*—Thick; leathery; with inside velvety and outside satiny.

*Shape.*—Outside: broadly obovate; scalloped with 1 to 2 notches. Intermediate: obovate-cuneate; scalloped with 1 to 2 notches. Inside: obovate-cuneate; scalloped with 1 to 2 notches.

*Color.*—Colors may be modified by being shaded and/or washed or tinted with other colors.

This description of a newly opened flower was made from a rose grown outdoors in the month of October, at Ontario, California:

*Color.*—*Outside petal*—outside surface: near Crimson, Plate 22, page 22, with a spot of Canary Yellow, Plate 2/2, page 2, at base of petal shading to Canary Yellow, Plate 2/3, page 2; inside surface: near Cardinal Red, Plate 822/2, page 168, with a spot of Aureolin, Plate 3/1, page 3, at base of petal. *Intermediate petal*—outside surface: near Rose Madder, Plate 23, page 23, with a spot of Canary Yellow, Plate 2/2, page 2, at base of petal shading to Canary Yellow, Plate 2/3, page 2; inside surface: near Cardinal Red, Plate 822/2, page 168, with a spot of Aureolin, Plate 3/1, page 3, at base of petal. *Inner petal*—outside surface: near Rose Madder, Plate 23, page 23, with a spot of Canary Yellow, Plate 2/2, page 2, at base of petal shading to Canary Yellow, Plate 2/3, page 2; inside surface: near Cardinal Red, Plate 822/1, page 168, with a spot of Aureolin, Plate 3/1, page 3, at base of petal.

This description was made from a rose that was open for three days indoors in the month of October, at Ontario, California:

*Color.*—*Outside petal*—outside surface: near Tyrian Rose, Plate 24, page 24, with a spot of Canary Yellow, Plate 2/2, page 2, at base of petal shading to Canary Yellow, Plate 2/3, page 2; inside surface: near Cardinal Red, Plate 822/3, page 168, with a spot of Canary Yellow, Plate 2/2, page 2, at base of petal. *Inside petal*—outside surface: near Rose Madder, Plate 23, page 23, with a spot of Canary Yellow, Plate 2/2, page 2, at base of petal shading to Canary Yellow, Plate 2/3, page 2; inside surface: near Cardinal Red, Plate 822/2, page 168, with a spot of Aureolin, Plate 3/1, page 3, at base of petal.

*General color effect.*—Newly opened flower—near Cardinal Red, Plate 822/2, page 168. Three days open—near Cardinal Red, Plate 822/3, page 168.

*Behavior.*—Drop off cleanly; fading only slightly; slightly affected by hot, dry weather by fading to lighter shade of red.

*Flower longevity.*—On bush in garden—3 days in October. Cut roses grown outdoors kept at living room temperatures—3 to 4 days in October.

*Reproductive organs*

Stamens: Medium to many; from 40 to 50 in number; arranged regularly about pistils.

Filaments: Long, from 7 to 15 mm. in length; most with anthers. *Color*—near Tangerine Orange, Plate 9/1, page 9, washed with Mandarin Red, Plate 17/1, page 17.

Anthers: Medium to large; all open at once. *Color*—near Indian Yellow, Plate 6/2, page 6, becoming tinted with Mandarin Red, Plate 17/2, page 17.

Pollen: Moderate to abundant. *Color*—Yellow Ochre, Plate o7, page 101.

Pistils: Many; from 60 to 70 in number.

Styles: Uneven; medium to long, from 5 to 10 mm. long; thin; loosely bunched. *Color*—near Sulphur Yellow, Plate 1/3, page 1, at base becoming Crimson, Plate 22, page 22, at upper end.

Stigma: Color—translucent but near Aureolin, Plate 3/3, page 3.

Ovaries: All protruding from calyx.

Hips: Under normal conditions this variety does not set seed so the hips do not mature.

Sepals: Falling soon; moderately long; curled. *Color*—inside: near Citron Green, Plate XXXI (Ridgway), becoming washed with Fawn Color, Plate XL (Ridgway); outside: near Lime Green, Plate XXXI (Ridgway), becoming washed with Cinnamon-Buff, Plate XXIX (Ridgway).

Seeds: Normally does not set seed.

*Plant*

Foliage:

*Leaves.*—Compound of 5 to 7 leaflets; moderately abundant; medium to large; heavy to leathery; semi-glossy.

*Leaflets.*—Shape—oval to ovate, with apex acute; base round; margin doubly serrate.

*Color.*—*Mature*—upper surface: near Yew Green, Plate XXXI (Ridgway); under surface: near Asphodel Green, Plate XLI (Ridgway). *Young*—upper surface: near Absinthe Green, Plate XXXI (Ridgway), washed with Mineral Red, Plate XXVII (Ridgway); under surface: near Absinthe Green, Plate XXXI (Ridgway), washed with Dark Mineral Red, Plate XXVII (Ridgway).

*Rachis.*—Medium in caliper. Upper side—grooved. Under side—moderately smooth to sparsely prickly.

*Stipules.*—Medium length; medium width; with moderately short points turning out at an angle of more than 45°, recurved toward the stem sometimes.

*Disease.*—Moderately resistant to mildew.

Growth:

*Habit.*—Bushy; upright; much branched.

*Growth.*—Very vigorous.

*Canes.*—Moderately heavy.

*Main stems.*—Color—near Light Cress Green, Plate XXXI (Ridgway). *Large prickles*—several to many; long; hooked downward; with short narrow base. Color—near Vandyke Brown, Plate XXVIII (Ridgway). *Small prickles*—few. Color—near Vandyke Brown, Plate XXVIII (Ridgway). *Hairs*—none.

*Branches.*—Color — near Rainette Green, Plate XXXI (Ridgway). *Large prickles*—several; long; hooked downward; with short narrow base. Color—near Snuff Brown, Plate XXIX (Ridgway). *Small prickles*—few. Color—near Snuff Brown, Plate XXIX (Ridgway). *Hairs*—none.

*New shoots.*—Color—near Absinthe Green, Plate XXXI (Ridgway), washed with Mineral Red, Plate XXVII (Ridgway). *Large prickles* — several; long; hooked downward; with short narrow base. Color—near Vandyke Red, Plate XIII (Ridgway). *Small prickles*—few. Color—near Vandyke Red, Plate XIII (Ridgway). *Hairs*—none.

I claim:

A new and distinct variety of rose plant characterized as to novelty by the exceptionally large size of the flowers for red roses; by the entirely new shade of red color in the bud and newly opened bloom and more particularly distinctive in the class of double roses; by the exceptional length of the flower bud as the first petal opens and the unusual length of the peduncle; and by by the exceptionally vigorous plant on which the flowers are produced singly on stems of greater than average length, substantially as shown and described.

HERBERT C. SWIM.

No references cited.